(12) United States Patent
Gaur et al.

(10) Patent No.: US 9,914,684 B2
(45) Date of Patent: Mar. 13, 2018

(54) FEED SOURCES FOR ALLYL ALCOHOL PRODUCTION PROCESSES

(71) Applicant: Lyondell Chemical Technology, L.P., Houston, TX (US)

(72) Inventors: Sarthak Gaur, Houston, TX (US); Beaven S. Mandimutsira, Sugar Land, TX (US); Daniel F. White, Houston, TX (US); Walter S. Dubner, Wilmington, DE (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/352,771

(22) Filed: Nov. 16, 2016

(65) Prior Publication Data

US 2017/0144953 A1    May 25, 2017

Related U.S. Application Data

(60) Provisional application No. 62/258,203, filed on Nov. 20, 2015, provisional application No. 62/421,659, filed on Nov. 14, 2016.

(51) Int. Cl.
| | | |
|---|---|---|
| *C07C 29/56* | (2006.01) | |
| *C07C 29/80* | (2006.01) | |
| *C07C 29/141* | (2006.01) | |
| *C07C 45/50* | (2006.01) | |

(52) U.S. Cl.
CPC ............ *C07C 29/56* (2013.01); *C07C 29/141* (2013.01); *C07C 45/50* (2013.01)

(58) Field of Classification Search
CPC ....... C07C 29/56; C07C 29/141; C07C 29/80; C07C 45/505
See application file for complete search history.

(56) References Cited

U.S. PATENT DOCUMENTS

| | | |
|---|---|---|
| 3,238,264 A | 3/1966 | Rowton |
| 5,262,371 A | 11/1993 | Faraj |
| 5,426,250 A * | 6/1995 | Chen ...................... C07C 29/16 568/862 |
| 6,803,491 B1 | 10/2004 | Shum |
| 7,847,135 B1 | 12/2010 | White |

FOREIGN PATENT DOCUMENTS

| | | |
|---|---|---|
| WO | WO-2005049201 A1 | 6/2005 |
| WO | WO-2011053671 A1 | 5/2011 |

OTHER PUBLICATIONS

The International Search Report and Written Opinion for PCT/US2016/062217 dated Feb. 23, 2017.

* cited by examiner

*Primary Examiner* — Sikarl A Witherspoon (57) ABSTRACT

Allyl alcohol production processes are generally described herein. One or more of the processes generally include contacting a propylene oxide stream with an isomerization catalyst under isomerization conditions sufficient to form an isomerization product stream including allyl alcohol, wherein the propylene oxide stream includes a total impurity concentration of at least 100 ppm. One or more of the processes generally includes purging at least a portion of a stream from one or more separation unit(s).

15 Claims, 3 Drawing Sheets

FEED SOURCES FOR ALLYL ALCOHOL PRODUCTION PROCESSES

CROSS-REFERENCE TO RELATED APPLICATIONS

This application claims the benefit of priority to U.S. Provisional Application No. 62/258,203, filed on Nov. 20, 2015, and U.S. Provisional Application No. 62/421,659, filed on Nov. 14, 2016. Each patent application identified above is incorporated here by reference in its entirety.

STATEMENT REGARDING FEDERALLY SPONSORED RESEARCH OR DEVELOPMENT

Not applicable.

FIELD

The present disclosure generally relates to the production of allyl alcohol. In particular, embodiments contained herein relate to feed sources for allyl alcohol production processes.

BACKGROUND

This section introduces information that may be related to or provide context for some aspects of the techniques described herein and/or claimed below. This information is background facilitating a better understanding of that which is disclosed herein. Such background may include a discussion of "related" art. That such art is related in no way implies that it is also "prior" art. The related art may or may not be prior art. The discussion is to be read in this light, and not as admissions of prior art.

Allyl alcohol production processes generally include contacting a propylene oxide stream with an isomerization catalyst to form allyl alcohol. Crude (i.e., unpurified) propylene oxide streams generally contains a significant level of impurities. Such impurities have generally been separated from the propylene oxide prior to use in subsequent processes, such as allyl alcohol production processes. However, the impurities can be difficult to separate from the propylene oxide itself. Moreover, further purification of propylene oxide may come at an expense of increased separation costs.

Contained herein are embodiments directed to resolving, or at least reducing, one or all of the problems mentioned above.

SUMMARY

The present disclosure generally includes allyl alcohol production processes. The processes generally include contacting a propylene oxide stream with an isomerization catalyst under isomerization conditions sufficient to form an isomerization product stream including allyl alcohol, wherein the propylene oxide stream includes a total impurity concentration of at least 100 ppm.

One or more embodiments include the process of the preceding paragraph and further include recovering allyl alcohol from the isomerization product stream.

One or more embodiments include the process of any preceding paragraph, wherein the propylene oxide stream contacts the isomerization catalyst within an isomerization reactor and the recovering includes introducing the isomerization product stream into a first column adapted to separate methanol from allyl alcohol and form a first overhead stream including methanol and propylene oxide and a first bottoms stream including allyl alcohol; transferring the first overhead stream to a second column adapted to separate methanol from propylene oxide and form a second overhead stream including propylene oxide and a second bottoms stream including methanol; and transferring the second overhead stream to the isomerization reactor.

One or more embodiments include the process of any preceding paragraph, wherein the recovering includes introducing the isomerization product stream into a first column adapted to separate propylene oxide from allyl alcohol and form a first overhead stream including propylene oxide and a first bottoms stream including allyl alcohol; and transferring the first bottoms stream to a second column adapted to separate methanol from allyl alcohol and form a second overhead stream including methanol and a second bottoms stream including allyl alcohol.

One or more embodiments include the process of any preceding paragraph, wherein the first bottoms stream includes less than 25 ppm methanol.

One or more embodiments include the process of any preceding paragraph, wherein the second bottoms stream includes less than 25 ppm methanol.

One or more embodiments include the process of any preceding paragraph, wherein the propylene oxide stream includes a methyl formate concentration in a range of 0 wt. % to 1 wt. % based on the total weight of the propylene oxide stream.

One or more embodiments include the process of any preceding paragraph, wherein the isomerization product stream includes an isomerization product methyl formate concentration that does not exceed the propylene oxide stream methyl formation concentration.

One or more embodiments include the process of any preceding paragraph, wherein the propylene oxide stream includes a methanol concentration in a range of 0 wt. % to 5 wt. % based on the total weight of the propylene oxide stream.

One or more embodiments include the process of any preceding paragraph, wherein the isomerization product stream includes an isomerization product methanol concentration that does not exceed the propylene oxide stream methanol concentration.

One or more embodiments include the process of any preceding paragraph, wherein the propylene oxide stream includes an acetone concentration in a range of 0 wt. % to 20 wt. % based on the total weight of the propylene oxide stream.

One or more embodiments include the process of any preceding paragraph, wherein the propylene oxide stream includes a water concentration in a range of 0 wt. % to 5 wt. % based on the total weight of the propylene oxide stream.

One or more embodiments include the process of any preceding paragraph, wherein the propylene oxide stream includes a propionaldehyde concentration in a range of 0 wt. % to 1 wt. % based on the total weight of the propylene oxide stream.

One or more embodiments include the process of any preceding paragraph, wherein the propylene oxide stream includes a methyl formate concentration of at least 0.6 wt. % based on the total weight of the propylene oxide stream, a methanol concentration of at least 0.0032 wt. % based on the total weight of the propylene oxide stream, an acetone concentration of at least 0.03 wt. % based on the total weight of the propylene oxide stream, a water concentration of at least 0.16 wt. % based on the total weight of the propylene oxide stream, a propionaldehyde concentration of at least 0.0005 wt. % based on the total weight of the propylene oxide stream or combinations thereof.

One or more embodiments include the process of any preceding paragraph, wherein the isomerization conditions include an isomerization temperature in a range of 200° C. to 300° C. and an isomerization pressure in a range of 0 psig (0 Pa) to 30 psig (206,843 Pa).

One or more embodiments include the process of any preceding paragraph, wherein the isomerization catalyst includes lithium phosphate.

One or more embodiments include the process of any preceding paragraph, wherein the isomerization catalyst is suspended in a high boiling oil.

One or more embodiments include the process of any preceding paragraph, further including recovering allyl alcohol from the isomerization product stream to form an allyl alcohol stream; contacting the allyl alcohol stream with a hydroformylation catalyst in the presence of a gas stream including carbon monoxide and hydrogen under hydroformylation conditions sufficient to form a hydroformylation product including a butane diol intermediate; and contacting the butane diol intermediate with hydrogenation catalyst in the presence of hydrogen under hydrogenation conditions sufficient to form a hydrogenation product stream including 1,4 butane diol.

One or more embodiments include the process of the preceding paragraph, wherein the recovering allyl alcohol includes separating methanol from the allyl alcohol to form the allyl alcohol stream, wherein the allyl alcohol stream includes less than 25 ppm methanol.

One or more embodiments include the process of any preceding paragraph, wherein the process further includes introducing an impure propylene oxide stream into the first column, wherein the impure propylene oxide stream comprises a total impurity concentration of at least 100 ppm.

One or more embodiments include the process of any preceding paragraph, wherein the first column comprises a top, a bottom, and in the range of 36 to 49 theoretical stages, and wherein the impure propylene oxide stream is introduced to the first column at one or more theoretical stages each being in the range of the $17^{th}$ to the $28^{th}$ theoretical stage, counted from the bottom to the top of the first column.

One or more embodiments include the process of any preceding paragraph, wherein the process further includes purging at least a portion of the first overhead stream to form a first purge stream when the concentration of propylene oxide in the first overhead stream is 90 wt. % or less, based on the total weight of the first overhead stream.

One or more embodiments include the process of any preceding paragraph, wherein the purging step is a continuous or batch operation.

One or more embodiments include the process of the preceding paragraph and further include recovering allyl alcohol from the isomerization product stream. The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

While multiple embodiments are disclosed, still other embodiments will become apparent to those skilled in the art from the following detailed description. As will be apparent, certain embodiments, as disclosed herein, are capable of modifications in various obvious aspects, all without departing from the spirit and scope of the claims as presented herein. Accordingly, the drawings and detailed description are to be regarded as illustrative in nature and not restrictive.

BRIEF DESCRIPTION OF THE DRAWINGS

The claimed subject matter may be understood by reference to the following description taken in conjunction with the accompanying drawings, in which like reference numerals identify like elements, and in which:

While the claimed subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope as defined by the appended claims.

DETAILED DESCRIPTION

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. Further, various ranges and/or numerical limitations may be expressly stated below. It should be recognized that unless stated otherwise, it is intended that endpoints are to be interchangeable with one another to form additional ranges that may or may not be expressly stated herein. Further, any ranges include iterative ranges of like magnitude falling within the expressly stated ranges and are further understood to set forth every number and range encompassed within the broader range of values. Further, in the description below, unless otherwise specified, all compounds described herein may be substituted or unsubstituted and the listing of compounds includes derivatives thereof.

Propylene oxide (PO) is a valuable chemical that can be used to produce a variety of other chemicals, including, but not limited to, propylene glycol, propylene glycol ethers, 1,4 butane diol (BDO), and polyols, for example. Processes for producing propylene oxide are known in the art and, as such, are not discussed in detail herein. However, one process of forming propylene oxide generally includes reacting propylene with an oxidizing agent in the presence of a catalyst. Non-limiting examples of the oxidizing agent include organic hydroperoxides (e.g., ethyl benzene hydroperoxide, cumene hydroperoxide and tert-butyl hydroperoxide) and hydrogen peroxide, for example. Non-limiting examples of the catalyst include solubilized molybdenum catalysts, heterogeneous titania-on-silica catalysts, and titanium silicate catalysts, for example.

Propylene oxide streams produced from such processes generally contain a significant concentration of impurities. Impurities are defined herein as any component in a process stream other than the targeted product itself (e.g., propylene oxide is the targeted product in the propylene oxide streams). For example, the impurities present in propylene oxide streams may include water, hydrocarbons (e.g., $C_4$-$C_6$ hydrocarbons), and oxygen-containing compounds (e.g., propionaldehyde, methanol, acetone, methyl formate and aldehydes) as well as additional compounds other than the propylene oxide, depending on the specific process.

Such impurities have generally been separated from the propylene oxide prior to use in subsequent processes. Such separation processes are known in the art and generally include separating one or more of the impurities from the propylene oxide within a process stream (wherein the process stream is generally referred to as "impure propylene oxide") to form purified propylene oxide via one or more methods, including, but not limited to, extraction, distillation, extractive distillation, caustic treatment, scavenging, adsorption and combinations thereof, for example. As used herein, the term "purified propylene oxide" generally refers to a propylene oxide stream having a propylene oxide concentration of at least 98 wt. % based on the total weight of the propylene oxide stream. It is to be noted that use of the term "propylene oxide stream" herein refers to any stream containing propylene oxide. The specific components and concentrations thereof present in the respective propylene oxide stream will be clear based on the referenced discussion thereof.

While many processes exist for the separation of the impurities, such processes can be difficult to implement and/or are costly. Thus, continuous efforts have been underway to improve and develop methods to separate these impurities from propylene oxide. However, embodiments described herein provide for use of impure propylene oxide streams in subsequent processes, and in particular, in isomerization processes to form allyl alcohol, without the need for purification of the propylene oxide stream prior to isomerization. For example, one or more embodiments include isomerization of one or more impure propylene oxide streams in the presence of an isomerization catalyst under isomerization conditions to form an isomerization product including allyl alcohol. As utilized herein, "impure propylene oxide streams" are defined as propylene oxide streams having a total impurity concentration of at least 100 ppm. The impure propylene oxide stream(s) may include crude propylene oxide streams as well as other propylene oxide streams including the specified total impurity concentration.

While it is noted that the term "impurities" generally include one or more individual, discrete impurity components, each specified concentration range for each separate impurity component may include a concentration in a range of 0 wt. % to an upper limit. While in view of each discrete impurity component concentration recited it may appear that the total impurity concentration may be 0 wt. %, it would be obvious to one skilled in the art that with a specified total impurity concentration of at least 100 ppm (or as otherwise noted herein for any particular process stream within the processes discussed herein), every discrete impurity component could not be present in the specified process stream, such as the impure propylene oxide stream, at a level lower than that such that the specified process stream has a total impurity concentration less than that specified (e.g., at least 100 ppm in the case of the impure propylene oxide stream). However, each discrete impurity component may or may not be present in the specified process stream.

Thus, in one more embodiments, the impure propylene oxide stream may include methyl formate at a methyl formate concentration in a range of 0 wt. % to 1 wt. %, or at least 0.06 wt. %, or 0.2 wt. % to 0.5 wt. % based on the total weight of the impure propylene oxide stream, for example. The impure propylene oxide stream may include methanol at a methanol concentration in a range of 0 wt. % to 5 wt. %, or at least 0.0032 wt. %, or at least 0.1172 wt. %, or 0.0001 wt. % to 1 wt. % based on the total weight of the impure propylene oxide stream, for example. The impure propylene oxide stream may include acetone at an acetone concentration in a range of 0 wt. % to 20 wt. %, or at least 0.03 wt. %, or 1 wt. % to 10 wt. % based on the total weight of the impure propylene oxide stream, for example. The impure propylene oxide stream may include water at a water concentration in a range of 0 wt. % to 5 wt. %, or at least 0.16 wt. %, or 0.4 wt. % to 3 wt. % based on the total weight of the impure propylene oxide stream, for example. The impure propylene oxide stream may include propionaldehyde at a propionaldehyde concentration in a range of 0 wt. % to 1 wt. %, or at least 0.0005 wt. %, or 0.01 wt. % to 0.8 wt. % based on the total weight of the impure propylene oxide stream, for example. The impure propylene oxide stream may include 2-methylpentane at a 2-methylpentane concentration in a range of 0 wt. % to 5 wt. %, or 0.01 wt. % to 0.8 wt. %, or in an amount of at least 0.0005 wt. %, based on the total weight of the impure propylene oxide stream, for example.

As discussed above, the isomerization processes generally include contacting the impure propylene oxide stream with an isomerization catalyst under isomerization conditions to form an isomerization product including allyl alcohol. Isomerization processes are known in the art and generally include slurry and/or gas phase processes. However, one or more embodiments include slurry phase isomerization. In slurry phase isomerization, the isomerization catalyst is suspended in an inert liquid (i.e., to form a catalyst slurry) and the propylene oxide is introduced to the catalyst slurry to react and form allyl alcohol. The inert liquid may include any suitable hydrocarbon or mixture thereof which will remain liquid, and is non-reactive and thermally stable, at the isomerization conditions employed. Illustrative, non-limiting examples of the inert liquid include high boiling temperature oils (i.e., those having a boiling temperature greater than the isomerization temperature) including, but not limited to $C_{12}$ or greater alkylaromatic hydrocarbons, such as dodecyl benzene or mixtures of alkylaromatic hydrocarbons, such as $C_{14}$-$C_{30}$ alkylaromatic hydrocarbons (e.g., Therminol*55, a product of Solutia, Inc.), for example.

Isomerization catalysts are known in the art and illustrative, non-limiting examples generally include lithium phosphate catalysts. For example, the lithium phosphate catalysts may include lithium phosphate supported on an inert supporting material. An inert supporting material is one, which itself, does not catalyze under isomerization conditions. Such inert support materials may include talc, inorganic oxides, clays and clay minerals, ion-exchanged layered compounds, diatomaceous earth compounds, zeolites, resinous support materials, such as a polyolefin, or combinations thereof, for example. Specific inorganic oxides include silica, alumina, magnesia, titania, zirconia and combinations thereof (e.g., silica-alumina and aluminosilicates), for example.

The isomerization catalyst may include lithium phosphate and optional inert support in any amount desired for the isomerization reaction. However, in one or more embodiments, wherein the isomerization catalyst includes the inert support, the isomerization catalyst may include a lithium phosphate concentration in a range of 5 wt. % to 60 wt. %, or 10 wt. % to 55 wt. %, or 15 wt. % to 75 wt. % and a support concentration in a range of 40 wt. % to 95 wt. %, or 45 wt. % to 90 wt. %, or 25 wt. % to 85 wt. %, based on the total weight of isomerization catalyst.

In addition, the lithium phosphate catalyst may include additional components, such as sodium, boron or combinations thereof, for example. For example, the lithium phosphate catalyst may include boron in a boron concentration in a range of 0.03 wt. % to 1 wt. %, or 0.1 wt. % to 0.8 wt. % based on the total weight of the lithium phosphate catalyst. The lithium phosphate catalyst may include sodium in a sodium concentration in a range of 0.01 wt. % to 1 wt. %, or 0.02 wt. % to 0.8 wt. % based on the total weight of the lithium phosphate catalyst, for example. The lithium phosphate catalyst may have a boron:lithium molar ratio in a range of 0.001:1 to 0.05:1, or 0.003:1 to 0.03:1, or 0.007:1 to 0.02:1, for example. The lithium phosphate catalyst may have a sodium:lithium molar ratio in a range of 0.0002:1 to 0.02:1, or 0.003:1 to 0.01:1, for example. See, U.S. Pat. No. 6,803,491, which is incorporated in its entirety herein.

In one or more embodiments, the isomerization catalyst may contact the impure propylene oxide stream in an amount in a range of 1 wt. % to 30 wt. %, or 4 wt. % to 20 wt. %, or 6 wt. % to 15 wt. % based on the total weight of the isomerization reaction mixture (e.g., the "isomerization reaction mixture" includes the components of the impure propylene oxide stream and the isomerization catalyst, as well as any other minor components known to ones skilled in the art), for example.

In practice, isomerization reaction conditions vary depending upon reaction parameters, reactor size and charge and the individual components employed. However, in one or more embodiments, the isomerization conditions may include an isomerization temperature in a range of 200° C. to 300° C., or 240° C. to 280° C., or 230° C. to 270° C., for example and an isomerization pressure in a range of 0 psig (0 Pa) to 30 psig (206,843 Pa), or 0 psig (0 Pa) to 15 psig (103,421 Pa), or 5 psig (34,474 Pa) to 10 psig (68,948 Pa), for example.

Embodiments of the technology provide for allyl alcohol production processes that exhibit propylene oxide conversion rates that are substantially similar to those utilizing purified propylene oxide. For example, the allyl alcohol production processes may exhibit a propylene oxide conversion rate in a range of 45% to 55%, or 40% to 60%, or 25% to 75%. The propylene oxide conversion can be used to evaluate the activity or efficiency of the catalyst and is generally calculated via the following equation: conversion (%)=propylene oxide reaction (wt.)/propylene oxide fed (wt.)*100. Embodiments of the technology further provide for allyl alcohol production processes exhibiting a selectivity that is substantially similar to those utilizing purified propylene oxide. For example, the allyl alcohol production processes may exhibit a selectivity in a range of 90% to 99%, or 91% to 98%, or 92% to 93%. The term "selectivity" refers to the percentage of input/reactant converted to a desired output/product (i.e., propylene oxide converted to allyl alcohol in the allyl alcohol production processes).

Isomerization processes may further include recovering the formed allyl alcohol from the isomerization product. As with other processes, the isomerization product may include a variety of impurities (e.g., as a result of side-chain reactions). For example, the impurities present in the isomerization product may include n-propanol, $C_{4+}$ hydrocarbons, $C_{1+}$ oxygenates, acrolein or combinations thereof, as well as other compounds other than the allyl alcohol, depending on the specific process. Furthermore, the isomerization product may include one or more of the same impurities as those present in the isomerization feed (e.g., as a result of unreacted feedstock). For example, the isomerization product may include propionaldehyde, water, acetone, acetaldehyde, 2-methylpentane, methyl formate or combinations thereof, for example.

Thus, recovery of the allyl alcohol may include, without limitation, separation and/or purification processes (including but not limited to flashing and distillation). Such separation processes are known in the art and generally include separating one or more of the impurities from the allyl alcohol within a process stream (generally referred to as "impure allyl alcohol") to form purified allyl alcohol via one or more methods, including, but not limited to extraction, distillation, extractive distillation, caustic treatment, scavenging, adsorption and combinations thereof, for example. As used herein, the term "purified allyl alcohol" generally refers to an allyl alcohol stream having an allyl alcohol concentration of at least 98 wt. % based on the total weight of the allyl alcohol stream. It is to be noted that use of the term "allyl alcohol stream" herein refers to any stream containing allyl alcohol. The specific components and concentrations thereof present in the respective allyl alcohol stream will be clear based on the referenced discussion thereof.

One or more specific embodiments include staged separation of one or more of the impurities from the allyl alcohol. The staged separation can include any number of stages sufficient to achieve the target allyl alcohol concentration in an allyl alcohol stream (or alternatively, to achieve a target impurity concentration). For example, the staged separation may include a number of stages in a range of 2 to 10 stages or 2 to 5 stages or 2 to 4 stages, or 3 to 4 stages. In such staged separation processes, the allyl alcohol is generally separated from a variety of lighter boiling components in the upstream stages (i.e., stages prior to the final stage) of the separation process and separated from heavier boiling components in the final stage of the separation process (e.g., the allyl alcohol is separated from heavier boiling components via the final overhead stream).

However, it has been determined that when utilizing an allyl alcohol stream formed from the processes described herein (i.e., those utilizing impure propylene oxide as feed for the allyl alcohol production process) in subsequent processes (e.g., BDO production processes), separation of any remaining acetaldehyde and methyl formate from the allyl alcohol may be unnecessary when the concentration of such components in the isomerization product does not exceed the concentration of such components in the impure propylene oxide stream. However, one or more embodiments do include separation of methanol from the propylene oxide prior to subsequent use of the allyl alcohol stream. In one or more embodiments, the staged separation includes separation of methanol from the allyl alcohol in a second stage of the separation process. For example, the methanol may be separated from the allyl alcohol via a second overhead stream. Alternatively, the methanol may be separated from the allyl alcohol in a first stage of the separation process. In such embodiments, the methanol is generally separated from the allyl alcohol in a first overhead stream, along with a number of additional components, which may be recycled back to the isomerization reaction. As such, the separation process may include an additional stage (e.g., stage 1A) adapted to separate the methanol from the remainder of the components in the first overhead stream.

In one or more embodiments, the target allyl alcohol concentration includes less than 5 wt. %, or less than 3 wt. %, or less than 1 wt. % propylene oxide based on the total weight of the allyl alcohol stream and less than 100 ppm, or less than 50 ppm, or less than 25 ppm methanol, based on the total weight of the allyl alcohol stream. It will be within the capabilities of the skilled artisan to adjust separation conditions as needed to accomplish the above separations. In one or more embodiments, the target allyl alcohol concentration includes less than 5 wt. %, or less than 3 wt. %, or less than 1 wt. % propylene oxide based on the total weight of the allyl alcohol stream, less than 3 wt. %, or less than 1 wt. %, or less than 0.1 wt. % water based on the total weight of the allyl alcohol stream, and less than 100 ppm, or less than 50 ppm, or less than 25 ppm propionaldehyde, based on the total weight of the allyl alcohol stream. It will be within the capabilities of the skilled artisan to adjust separation conditions as needed to accomplish the above separation(s).

Many commercial processes utilize allyl alcohol for the manufacture of 1,4 butanediol (BDO) (referred to herein interchangeably with "butane diol production processes"). Allyl alcohol may also be used as a hydroxyl functional monomer in the polymer industry. For instance, allyl alcohol can be used for producing styrene-allyl alcohol copolymers and hydroxyl acrylic resins, for example.

Butane diol production processes may include a hydroformylation reaction followed by hydrogenation. In the hydroformylation reaction, allyl alcohol (fed to the reaction via an allyl alcohol stream) is generally contacted with a hydroformylation catalyst in the presence of a gas stream, such as a $CO/H_2$ gas mixture, under hydroformylation conditions sufficient to form a hydroformylation product including a BDO intermediate. The BDO intermediate may include a variety of components. Such components will vary depending upon the specific hydroformylation conditions and components of the allyl alcohol stream. However, in one or more embodiments, the BDO intermediate includes 4-hydroxybutyraldehyde.

The hydroformylation reaction may occur in the presence of a solvent. Solvents may include, but are not limited to those that are capable of solubilizing the hydroformylation catalyst but not reactive to other components produced in the hydroformylation reaction. Illustrative, non-limiting examples of solvents include compounds having low or minimal solubility in water, such as $C_4$-$C_{20}$ aliphatic hydrocarbons, $C_6$-$C_{20}$ aromatic hydrocarbons, $C_6$-$C_{20}$ halogenated aromatic hydrocarbons and ethers, such as toluene, cyclohexane and methyl t-butyl ether, for example.

Hydroformylation catalysts are known in the art and illustrative, non-limiting examples generally include Rhodium based catalysts, for example. The hydroformylation catalyst may include Rhodium in a Rhodium concentration in a range of 10 ppm to 1000 ppm, or 50 ppm to 500 ppm, or 100 ppm to 200 ppm based on the total weight of the hydroformylation catalyst, for example. In one or more embodiments, the hydroformylation catalyst may include additional components, such as phosphine, for example. The hydroformylation catalyst may have a phosphine:rhodium molar ratio greater than 1:1, or greater than 1.2:1, or greater than 1.5:1, for example.

Rhodium based catalysts are known in the art and illustrative, non-limiting examples include $RhH(CO)_n(PR_3)_3$, $RhX(CO)_n (PR_3)_2$; $RhX(PR_3)_3$, wherein n is 1 or 2, X represents a halogen atom, $PR_3$ represents an organic tri-substituted phosphine and R represents an alkyl, aryl, alkoxy or aryloxy group, each R the same or different. Illustrative, non-limiting examples of tri-substituted phosphines include tributylphosphine, tricyclohexylphosphine, trioctylphosphine, triphenolphosphine, tritolylphospine, methyldiphenylphosphine, ethyl-n-pentylphenylphosphine, tributoxyphosphine and triphenoxyphosphine, for example.

In practice, hydroformylation reaction conditions vary depending upon reaction parameters, reactor size and charge and the individual components employed. However, in one or more embodiments, the hydroformylation conditions are fairly mild in an effort to favor the formation of linear rather than branched reaction products. For example, the hydroformylation conditions may include a hydroformylation temperature in a range of 20° C. to 100° C., or 60° C. to 80° C., or 60° C. to 70° C. and a hydroformylation pressure in a range of 20 psig (137,895 Pa) to 600 psig (4,136,854 Pa), or 30 psig (206,843 Pa) to 300 psig (2,068,427 Pa), or 35 psig (241,317 Pa) to 135 psig (930,792 Pa), for example.

The molar ratio of $CO:H_2$ contacting the hydroformylation catalyst may vary considerably, but in one or more embodiments may be about 1:1, or may be in a range of 1:3 to 3:1, or 1:9 to 9:1, for example. The reaction time for the hydroformylation reaction is such that the predominance of the allyl alcohol reacts.

Upon reaction and formation of the hydroformylation product, the hydroformylation catalyst may be separated from the BDO intermediate via known methods, such as extraction, to form a hydrogenation feed including the BDO intermediate, which may then be hydrogenated over a hydrogenation catalyst in the presence of hydrogen (and optional solvent) under hydrogenation conditions to form a hydrogenation product including the BDO.

Hydrogenation catalysts are known in the art and illustrative, non-limiting examples include Group VII metal catalysts. For example, Group VII metal catalysts may include nickel, cobalt, ruthenium, platinum, palladium, copper, zinc, chromium, alloys thereof or combinations thereof.

In one or more embodiments, the hydrogenation catalyst may contact the hydrogenation feed in an amount in a range of 0.1 wt. % to 15 wt. %, or 0.2 wt. % to 10 wt. %, or 0.3 wt. % to 3.3 wt. % based on the total weight of hydrogenation reaction mixture (e.g., the "hydrogenation reaction mixture" includes the components of the hydrogenation feed and the hydrogenation catalyst, as well as any other minor components known to ones skilled in the art), for example.

As briefly mentioned above, the hydrogenation may occur in the presence of solvent. Such solvent may be the same or different from those solvents previously described herein with reference to hydroformylation. When the same, such solvent may be added to the hydrogenation reaction or may be present in the hydrogenation feed as a result of the hydroformylation reaction.

In practice, hydrogenation reaction conditions vary depending upon reaction parameters, reactor size and charge and the individual components employed. However, in one or more embodiments, the hydrogenation conditions are more severe than those utilized for hydroformylation. For example, the hydrogenation temperature may be in a range of 60° C. to 200° C., or 80° C. to 140° C., or 90° C. to 110°

C. and the hydrogenation pressure may be in a range of 200 psig (1,378,951 Pa) to 1500 psig (10,342,136 Pa), or 300 psig (2,068,427 Pa) to 1250 psig (8,618,447 Pa), or 500 psig (3,447,379 Pa) to 1000 psig (6,894,757 Pa), for example. The reaction time for the hydrogenation reaction is such that the predominance of the BDO intermediate reacts.

Butane diol production processes may further include recovering the formed BDO from the hydrogenation product. Such recovery can be accomplished by methods which may include, without limitation, separation and/or purification processes (including, but not limited to, flashing, extraction and distillation). Such processes are known to ones skilled in the art and therefore are not described in detail herein.

Figure 1:
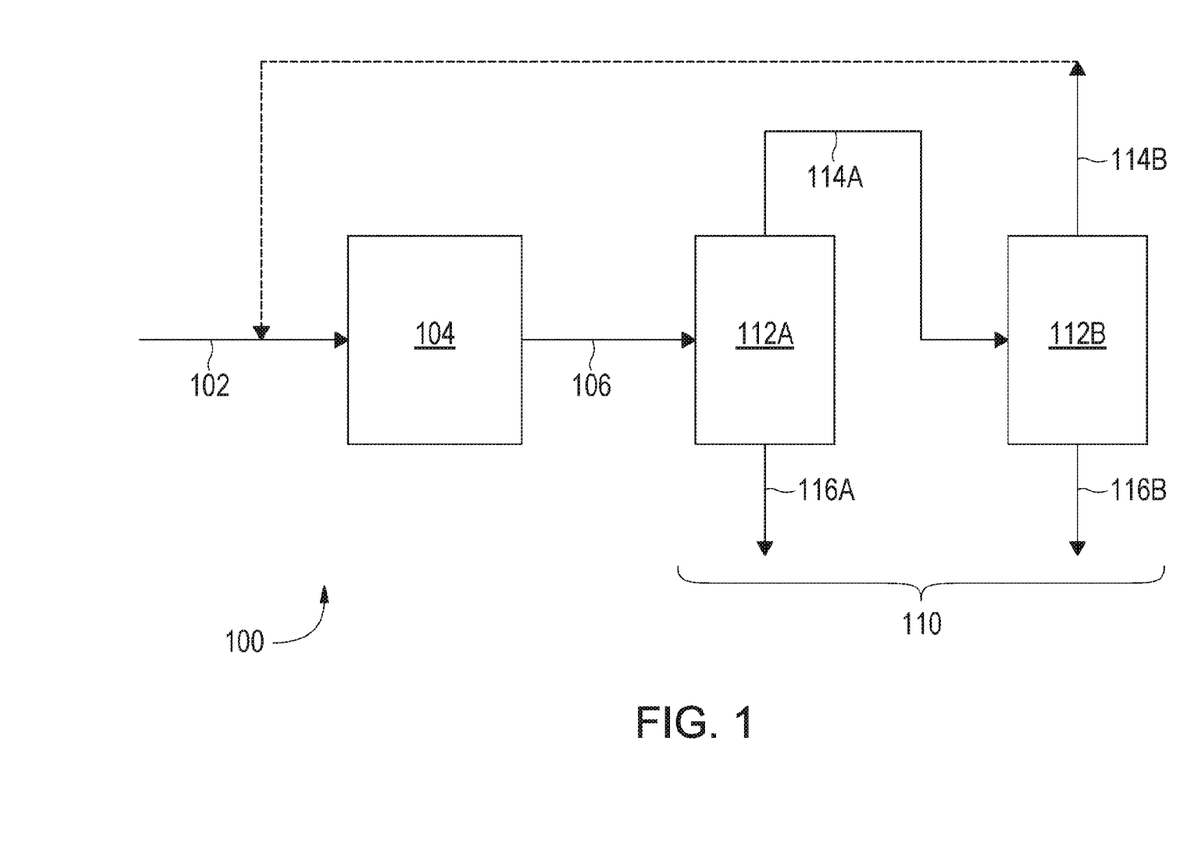
FIG. 1 illustrates a schematic of one or more embodiments of the disclosed processes.

FIG. 1 illustrates a schematic of an embodiment of a specific, non-limiting embodiment of an allyl alcohol production process 100. The allyl alcohol production process generally includes feeding a propylene oxide stream 102 to an isomerization reactor 104 having an isomerization catalyst disposed therein to form an isomerization product stream 106. The propylene oxide present in the propylene oxide stream 102 generally contacts the isomerization catalyst within the isomerization reactor 104 at isomerization conditions sufficient to form allyl alcohol, which is withdrawn from the isomerization reactor 104 via the isomerization product stream 106.

The allyl alcohol production process 100 further includes a separation zone 110. In the specific embodiment illustrated in FIG. 1, the separation zone 110 includes a first column 112A adapted to separate methanol via a first overhead stream 114A from the allyl alcohol, which is withdrawn from the first column 112A via the first bottoms stream 116A. The separation zone 110 may further include an additional column 112B adapted to separate methanol from lighter boiling components, such as propylene oxide, present in the first overhead stream 114A. Thus, first overhead stream 114A may be introduced to column 112B to form overhead stream 114B including lighter boiling components, such as propylene oxide, and bottoms stream 116B including methanol. Overhead stream 114B may optionally be recycled back to stream 102 for re-introduction to isomerization reactor 104. While not illustrated in FIG. 1, it is contemplated and within the skill in the art, that the separation zone 110 may include additional columns such that further separation may occur depending on the target allyl alcohol concentration.

Figure 2:
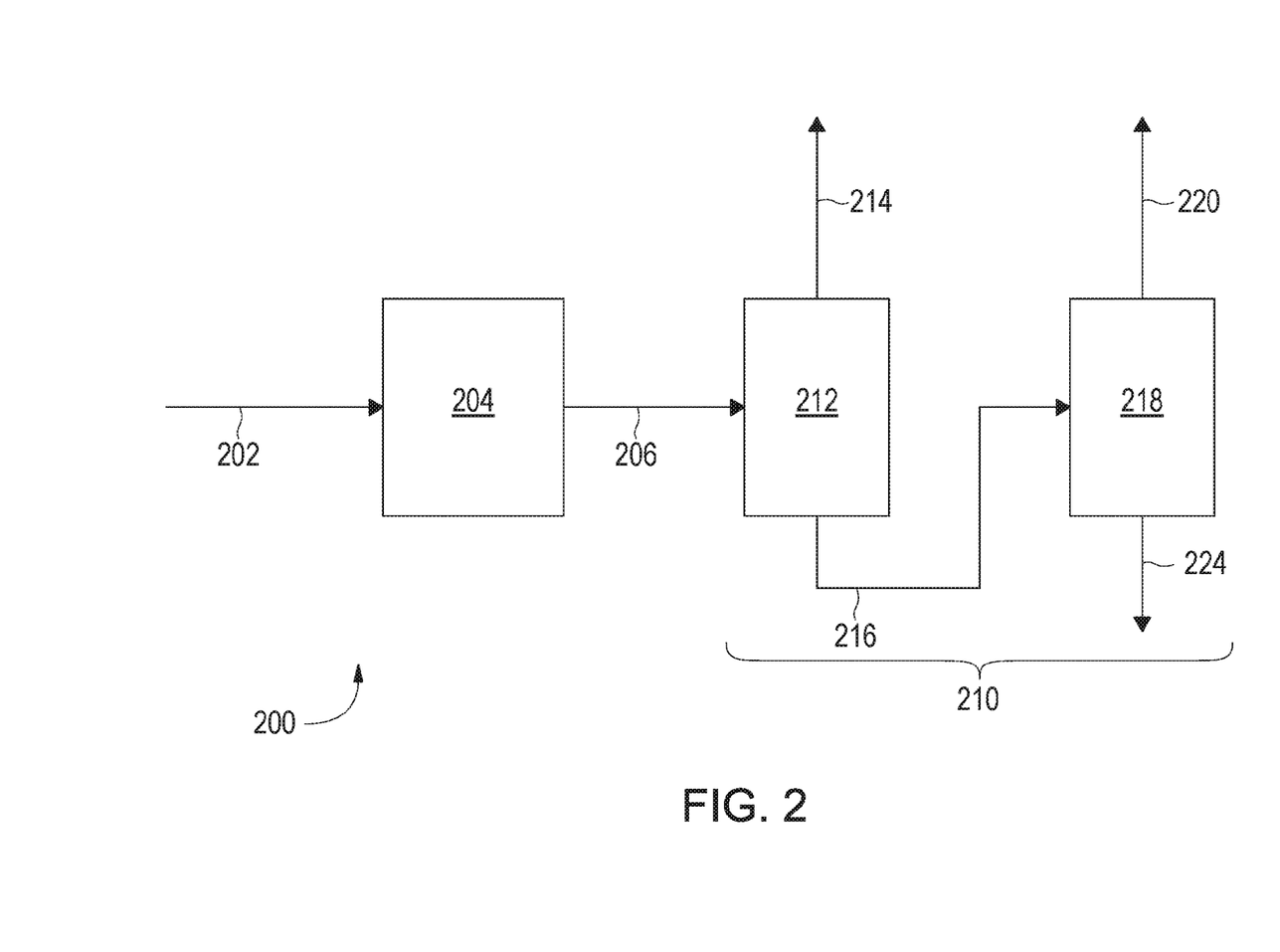
FIG. 2 illustrates a schematic of one or more embodiments of the disclosed processes.

FIG. 2 illustrates a schematic of an embodiment of a specific, non-limiting embodiment of an allyl alcohol production process 200. The allyl alcohol production process generally includes feeding a propylene oxide stream 202 to an isomerization reactor 204 having an isomerization catalyst disposed therein to form an isomerization product stream 206. The propylene oxide present in the propylene oxide stream 202 generally contacts the isomerization catalyst within the isomerization reactor 204 at isomerization conditions sufficient to form allyl alcohol, which is withdrawn from the isomerization reactor 204 via the isomerization product stream 206.

The allyl alcohol production process 200 further includes a separation zone 210. In the specific embodiment illustrated in FIG. 2, the separation zone 210 includes a first column 212 adapted to separate lighter boiling components, such as propylene oxide, via a first overhead stream 214 from the allyl alcohol, which is withdrawn from the first column 212 via the first bottoms stream 216. The first bottoms stream 216 is fed to a second column 218 adapted to separate methanol via a second overhead stream 220 from the allyl alcohol, which is withdrawn from the second column 218 via a second bottoms stream 224. While not illustrated in FIG. 2, it is contemplated and within the skill in the art, that the separation zone 210 may include additional columns such that further separation may occur depending on the target allyl alcohol concentration.

Figure 3:
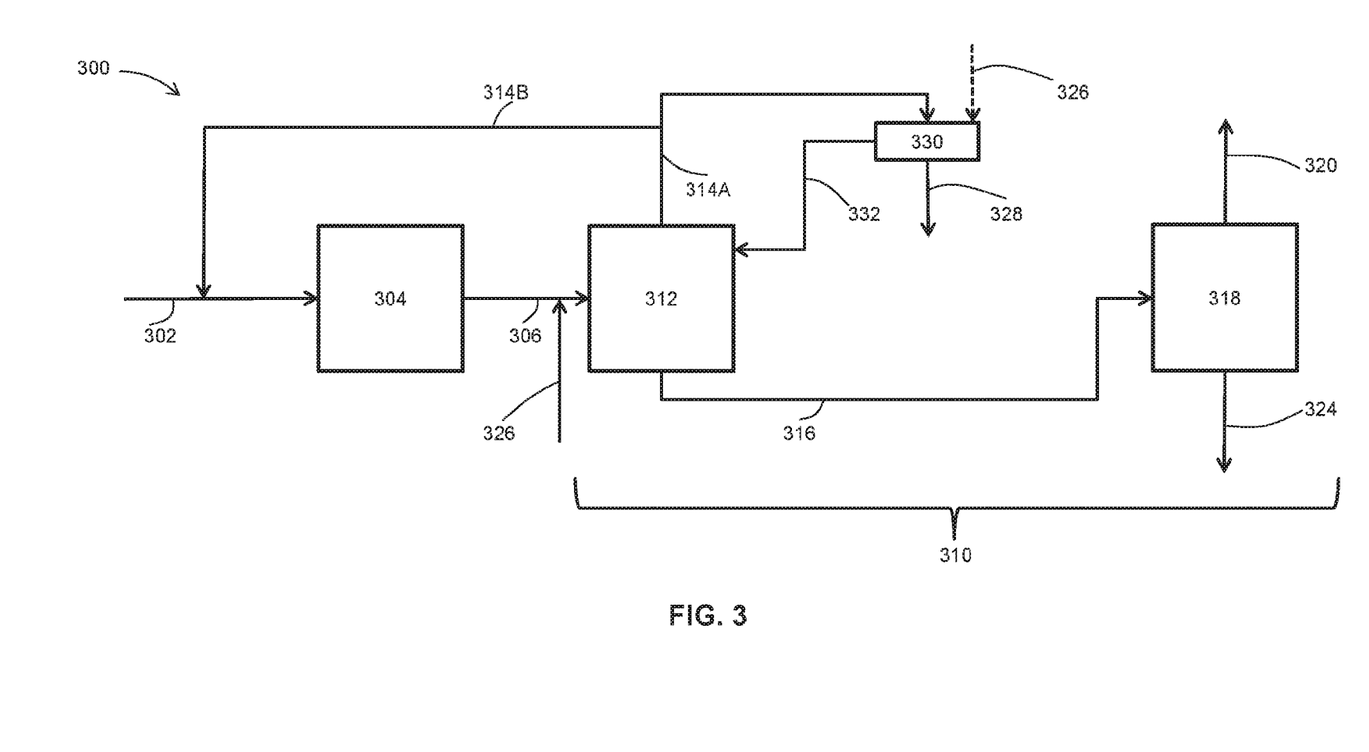
FIG. 3 illustrates a schematic of one embodiment of the disclosed process.

FIG. 3 illustrates a schematic of an embodiment of a specific, non-limiting embodiment of an allyl alcohol production process 300. The allyl alcohol production process generally includes feeding a propylene oxide stream 302 to an isomerization reactor 304 having an isomerization catalyst disposed therein to form an isomerization product stream 306. The propylene oxide present in the propylene oxide stream 302 generally contacts the isomerization catalyst within the isomerization reactor 304 at isomerization conditions sufficient to form allyl alcohol, which is withdrawn from the isomerization reactor 304 via the isomerization product stream 306.

The allyl alcohol production process 300 further includes a separation zone 310. In the specific embodiment illustrated in FIG. 3, the separation zone 310 includes a first column 312 adapted to separate lighter boiling components, such as propylene oxide, via a first overhead stream 314A from the allyl alcohol, which is withdrawn from the first column 312 via the first bottoms stream 316.

The allyl alcohol production process 300 further includes introducing an impure propylene oxide stream 326 into the first column 312, which in one or more embodiments comprises a top, a bottom, and in the range of 36 to 49 theoretical stages, or in the range of 41 to 44 theoretical stages. In one or more embodiments, the impure propylene oxide stream 326 is introduced to the first column 312 at one or more theoretical stages, each being in the range of the $17^{th}$ to the $28^{th}$ stage, or at one or more theoretical stages in each being in the range of the $19^{th}$ to the $25^{th}$ stage, counted from the bottom to the top of the first column 312. Introduction of the impure propylene oxide stream 326 at the above-mentioned location can provide a number of process advantages, including without limitation, for example, as shown in Table 6, enriching the amount of propylene oxide in the first overhead stream 314A and enriching the amount of water in the first bottoms stream 316. The impure propylene oxide stream 326 can be co-fed with the isomerization product stream 306 to the first column 312. In an alternative embodiment, the impure propylene oxide stream 326 (shown as a dashed line in FIG. 3) can be introduced to the first column 312 via a reflux drum 330. If the impure propylene oxide stream 326 is introduced to the first column 312 via a reflux drum 330, the impure propylene oxide stream 326 can be introduced to the reflux dream 330 and/or first column 312 in a number of process configurations, including without limitation, alone and/or co-fed (or otherwise mixed) with purified propylene oxide. At least a portion of the first overhead stream 314A optionally may be recycled back as a recycled stream 314B to stream 302 for re-introduction to isomerization reactor 304. Additionally, a reflux stream 332 taken from the reflux drum 330 may be introduced to the first column 312.

The allyl alcohol production process 300 can further include purging at least a portion of the first overhead stream 314A to form a first purge stream 328 comprising methanol, 2-methylpentane, propionaldehyde, water, and propylene oxide. The first purge stream 328 can be from the first overhead stream 314A or from the reflux drum 330 that is adapted to receive the first overhead stream 314A. In another aspect of the disclosure, the purging step occurs when the concentration of propylene oxide in the first overhead stream 328 reaches a desired amount, or reaches 90 wt. % or less, or reaches 85 wt. % or less, based on the total weight of the first overhead stream. Conversely, in another aspect of the disclosure, the purging step ends when the concentration of propylene oxide in the first overhead stream 328 is at or above the desired amount, or is 88 wt. % or more, or is 90 wt. % or more. The flow rate of the first purge stream 328 during the purging step is selected to reduce flooding in the first column and/or to achieve a predetermined concentration of propylene oxide in the first column overhead stream. For example, in one or more embodiments, the flow rate of the first purge stream 328 is in a range of 0 to 7000 lb/h (0-3175 kg/h), or in a range from 50 to 300 lb/h (23-136 kg/h).

The purging step can be a continuous or batch operation. For example, the first purge stream 328 can be removed continuously by using an online analyzer (e.g., a Process Gas Chromatograph) in conjunction with a final control element (e.g., a control valve such as a linear globe valve), where the control valve opens when the concentration of propylene oxide in the first overhead stream 328 is below a desired amount, and the control valve closes when the concentration is at or above the desired amount. The purging step can provide a number of process advantages including without limitation reduction of flooding at the one or more theoretical stages where the impure propylene oxide stream 326 is introduced to the first column 312, and maintenance of a desired propylene oxide concentration in the first overhead stream.

The first bottoms stream 316 is fed to a second column 318 adapted to separate lighter components such as, for example, propionaldehyde, acetone, methanol, 2-methylpentane, and water, via a second overhead stream 320 from the allyl alcohol, which is withdrawn from the second column 318 via a second bottoms stream 324. While not illustrated in FIG. 3, it is contemplated that the separation zone 310 may include additional columns such that further separation may carried out, depending on the desired allyl alcohol concentration.

EXAMPLES

To facilitate a better understanding of the disclosure, the following examples of embodiments are given. In no way should the following examples be read to limit, or to define, the scope of the appended claims.

Example 1

Four different propylene oxide streams of varying purity levels were isomerized by contact with lithium phosphate isomerization catalyst in Therminol-55® oil at 274° C. to form isomerization product streams. The isomerization included charging the oil to a glass beaker including a Teflon® coated stir bar and heating the oil over a hot plate until a temperature of 70° C. was attained. Lithium phosphate catalyst (6.5 g) was slowly added to the oil with stirring to prevent clumping of the catalyst powder. Once all of the powder had been added, the stirring and heating continued for a further time (ranging from 5-10 minutes depending on the sample) until full dispersion of the solid in the oil was obtained. The resulting slurry was then poured into the reactor through a metal funnel under a nitrogen stream flowing from the bottom of the reactor. The reactor consisted of an 18 cm, 30 mm internal diameter glass tube with a 3 neck 250 mL expansion flask attached at the top and a medium frit at the base. A glass to metal connector with bellows was attached at the top and a medium frit was attached at the base. A glass to metal connector with bellows was attached at the bottom of the reactor and was hooked up to a ¼" feed line and nitrogen feed. The reactor was than heated to 225° C. The propylene oxide stream was fed to the reactor at a rate of 20 mL/hour by passing through an evaporator coil at a temperature of 170° C. and combining the propylene oxide stream with the nitrogen stream to flow into the reactor through the frit at the bottom of the reactor. The nitrogen flow was maintained as heating continued to the isomerization temperature of 274° C. Once the temperature in the overhead distillation condenser attached to the reactor reached and stabilized over 50° C., nitrogen flow was discontinued leaving only the PO vapor stream going into the hot oil through the frit. Once the reactor temperature and the overhead temperature had stabilized (over a time of from 30-90 minutes depending on the sample), the glycol chilled product collection vessel was emptied through the drain valve at the bottom and the content discarded. The product vessel was drained every 1-2 hours into a pre-weighed bottle, which was cooled over dry ice prior to use. The mass of each product collected was obtained by weighing and subtracting the weight of the bottle. An aliquot of each sample was combined with 3-hydroxy THF as an internal standard and then analyzed by GC. Each run was continued for 48 hours with sampling every 2 hours.

Each propylene oxide stream (characterized as samples 1-4 in the Table below) was characterized by GC (gas chromatography) analysis, the results of which are illustrated in TABLE 1 below.

TABLE 1

|  | Sample 1 | Sample 2 | Sample 3 | Comparative |
| --- | --- | --- | --- | --- |
| Propylene Oxide | 88.73 | 97.83 | 99.93 | 99.90 |
| Water | 0.50 | 2.10 | 0.012 | <25 ppm |
| Methanol | 0.81 | 0.00 | 1 ppm | <25 ppm |
| Acetone | 8.30 | 0.00 | 7 ppm | <25 ppm |
| Methyl Formate | 0.30 | 0.00 | 292 ppm | <25 ppm |
| Propionaldehyde | 0.03 | 0.00 | 19 pm | <25 ppm |
| $C_{4+}$ Hydrocarbons | 0.73 | 0.07 | 1 ppm | 0.00 |
| $C_{4+}$ Oxygenates | 0.95 | 0.00 | 0.00 | 0.00 |

*Note:
All values are weight percent based on the total weight of the stream, with the exception as those identified as ppm Each isomerization product stream was characterized by GC (gas chromatography) analysis, the results of which are illustrated in TABLE 2 below.

TABLE 2

|  | Sample 1 | Sample 2 | Sample 3 | Comparative |
| --- | --- | --- | --- | --- |
| Propylene Oxide | 48.19 | 41.00 | 29.00 | 31.00 |
| Allyl Alcohol | 37.50 | 52.00 | 67.00 | 64.00 |
| Water | 0.67 | 2.313 | 0.243 | 0.263 |
| Methanol | 1.09 | 150 ppm | 274 ppm | 116 ppm |
| Acetone | 9.11 | 1.66 | 1.46 | 1.38 |
| Propionaldehyde | 0.69 | 0.60 | 0.60 | 0.70 |
| $C_{4+}$ Hydrocarbons | 0.47 | 0.00 | 0.00 | 0.00 |
| $C_{4+}$ Oxygenates | 1.21 | 0.60 | 0.60 | 0.40 |

*Note:
All values are weight percent based on the total weight of the stream, with the exception as those identified as ppm It was observed that sufficient conversion rates were obtained with the "impure propylene oxide" streams, while the resulting isomerization product streams further included levels of impurities that are not anticipated to significantly affect subsequent processes.

Example 2

Experiments were performed using an impure propylene oxide stream and introducing it as feed stock to a pilot-scale distillation tower. The HETP (Height Equivalent to Theoretical Plate) was determined using the results from the experiments. For example, a technique that was used to determine the HETP was to match results obtained from a simulation program (e.g., Aspen Plus® V7.3) with the analytical results from experiments. A reasonable match between the simulated and analytical data suggested that the assumed number of theoretical stages for separations in the simulation program was taken as equal to the actual number of stages present in the column. The match was deemed reasonable if the heavy and light key components in the analytical data and simulations matched within ±1 wt %. The heavy key and light key components in this case were allyl alcohol and propylene oxide, respectively.

The pilot-scale distillation tower was designed as a packed tower, furnished with electrically-powered reboiler, glycol/water cooled condensers, a feed vessel, and an overhead receiver. Electrically powered feed and reflux preheaters and post tube-in-tube coolers were installed for flexibility over a wide range of operating conditions. The tower was fabricated out of 2-inch (0.05 m) Schedule 40 SS-316 pipe. The tower included 3 cylindrical sections which were 4 foot (1.21 m), 1 foot (0.30 m), and 2 foot (0.60 m) in length, respectively. The sections were butt-welded on both ends with a 2-inch (0.05 m) 150# RF blind flange with 2.07-inch (0.052 m) ID. The tower was erected by stacking the sections over each other with the 4 foot (1.21 m) section at the top followed by the 1 foot (0.30 m) and 2 foot (0.60 m) sections, respectively. The flanges were held together by ⅝-inch (0.015 m) studs and nuts to secure the tower sections. The sections were packed with 0.24-inch (0.006 m) packing, which can be obtained from Canon Instrument Company having a business address of 2139 High Tech Road, State College, Pa. 16823, USA. To avoid blowing the packing out in the event of flooding, thick screen meshes were placed on top of the 4 foot (1.21 m), 1 foot (0.30 m), and 2 foot (0.60 m) tower sections, respectively. Three liquid redistributors supplied by Canon Instrument Company were inserted at three locations in each tower section to help redistribute the liquid and avoid wall effects that are typical in a separation column of this size. In addition, custom-designed flanges with hat-trays were installed at the top of 1 foot (0.30 m) section and at the bottom of 2 foot (0.60 m) section. Two flanges were used; one of them was sandwiched between the two-4 foot (1.21 m) and 1 foot sections and the other between the reboiler and bottom of 2 foot (0.60 m) section, respectively. The hat-trays were fabricated from a 10 mesh grating, folded in the shape of a cone, and tack-welded to the blind flange. The hat-tray flanges were designed to primarily avoid "choking" in the tower but to also serve as packing support and secondary liquid redistributor.

The pilot-scale distillation tower was designed with two feed locations, the primary feed point at the bottom of 4 foot (1.21 m) section and the secondary point at the bottom of 1 foot (0.30 m) section. The feed to the pilot-scale distillation tower was designed to flow across the feed-flange via a bore-through fitting with a ¼-inch (0.006 m) stainless steel tube swaged on the inside which terminated in the middle of the column. Table 3 summarizes the configuration and design for the pilot-scale distillation tower.

TABLE 3

| | |
|---|---|
| Total Packed Section | 78 inch (1.98 meter) |
| Feed Location (primary) | 32 inch (0.81 meter) from the bottom |
| Packing Hold-up | 0.20 gallon (0.76 liter) |
| Reboiler Hold-up | 1 gallon (3.78 liter) |
| Tower Hold-up | 1.2 gallon (4.54 liter) |

The process conditions used in the pilot-scale distillation tower for the experiments are shown in Table 4.

TABLE 4

| Parameter | | |
|---|---|---|
| Feed Flow | 1.44 lb/h | 0.65 kg/h |
| Distillate Flow | 1.03 lb/h | 0.47 kg/h |
| Bottoms Flow | 0.41 lb/h | 0.18 kg/h |
| Reflux Flow | 0.52 lb/h | 0.23 kg/h |
| Reflux Ratio (L/D) | 0.5 | 0.5 |
| Temp. of Overheads | 182.5° F. | 83.61° C. |
| Temp. of Bottoms | 298° F. | 147.78° C. |
| Temp. of Reflux Preheater | 75° F. | 23.89° C. |
| Temp. of Feed Preheater | 105° F. | 40.56° C. |

The pilot-scale distillation tower was designed was designed to operate in a tail-chase mode, i.e., the overhead and bottom product streams were recycled back to the tower feed. A 5 gallon (18.92 liter) feed vessel was chosen because it was deemed to provide the surge capacity that is required during operation and a specially-designed overheads vessel was used as the reflux drum to allow for the use of a level probe.

The level of the tower sump was cascaded to a control valve. Similarly, the level in the overhead receiver was designed to be cascaded to the distillate control valve, which was essentially a flow controller. The feed flow was controlled using a control valve. Three positive discharge gear pumps were installed to pump the feed, the distillate as well as reflux, and bottoms, respectively. To perform the mass balance for the tower feed, overhead, and bottom products, three process lines from the discharge of the three pumps were diverted to an online gas chromatographic analyzer, which, after analysis of the components, returned them back to the process line at the suction of the respective pump.

To perform dosing studies, which required the experiment to spike a chemical impurity in the system, three vessels with different volumes were designed. For smaller dosing amounts, a 300 mL hoke was designed which could be mounted on top of feed vessel via a quick-connect fitting, and contents transferred due to the pressure differential across the dosing vessel and feed vessel. Another pump was used to continuously mix the contents of feed vessel. The pump provided approximately 87 turnovers per hour, which ensured that feed and dosed chemical impurity were quickly mixed.

Nearly 1.5 gallon (5.67 liter) of the reactor effluent and approximately 0.5 gallon (1.89 liter) of impure propylene oxide stream, which were secured from 2 different production plants were first charged to the feed vessel for the pilot-scale distillation tower. Prior to feeding this mixture of chemicals to the tower for separation, the chemicals were mixed for approximately 2 hours to ensure that the composition was uniform. The contents in the feed vessel were pumped to the column sump and the sump then heated until the temperature of bottoms was about 298° F. (147.78° C.) and overheads were about 183° F. (83.88° C.). After reaching the desired temperature profile across the tower, the tower was operated in total reflux. To ensure that the tower was operating in total reflux, the level in reflux drum was maintained constant. At steady state, sample from overheads and bottoms was analyzed in the online analyzer. Upon ensuring that the overheads predominantly contain the light key and bottoms contain the heavy key, the tower was operated in tail chase mode, with a feed flow rate of 1.44 lb/h (0.65 kg/h), overhead flow rate of 1.03 lb/h (0.47 kg/h) and bottom flow rate of 0.41 lb/h (0.18 kg/h). Results for this experiment are shown in Table 5, and noted as analytical results.

Aspen Plus® V7.3 was used to perform simulations to obtain data from simulations to compare to the analytical results from the plant. A YIELD reactor (RYIELD), which is represented by Block 304 in FIG. 3, having a product which matched the temperature and pressure conditions of the reactor overhead, was used to model the isomerization reactor. A given component in the feed was "de-lumped" into a series of components in the product. This is suitable for a complex mix of reaction products where exact stoichiometric reactions are not evident. However, due to different levels of oxygenation and saturation of the various products, coupled with experimental and analytical error, an exact atom balance across the reaction may not be maintained.

The reaction model was derived from analytical results as follows:
 Calculate the weight fraction in the product minus weight fraction in the feed for each component.
 Assign components that increase in composition as yield products from components that decrease in composition.
  Four carbon products are assigned to isobutylene oxide and isobutene, which decreased in composition across the reactor
  All other components are assigned to propylene oxide; however
  Methanol was assigned to methyl formate. Methanol was observed with refined as well as impure propylene oxide feed, and the yield from propylene oxide is fixed at the experimental result using refined or impure propylene oxide feed with remaining methanol production from methyl formate.
 Divide the increase in component weight fraction by the weight fraction in the feed of its assigned source in the step above to get the yield to that component.

Not shown in FIG. 3 is a section of trays on top of the reactor, which was modeled as a RADFRAC with 4 theoretical stages along with a separate total condenser FLASH 2 block, with a vent. Vapor distillate from this block was split, with one stream refluxing back to the reactor and the other one feeding the first tower which is represented by block 312 in FIG. 3. The first tower was modeled as a RADFRAC with 41 theoretical stages with a separate total condenser FLASH 2 block, with a vent. The simulation modeled the recycle propylene oxide feed to the reactor as a split from vapor distillate of the first overheads stream 314A, The first bottoms stream 316 was simulated to feed a second tower 318, modeled as a RADFRAC containing 21 theoretical stages. Second bottoms stream 324 was simulated to feed a third tower, modeled as a RADFRAC containing 16 theoretical stages. The third overhead stream from the third tower represents the final allyl alcohol product.

For the simulations, the composition of feed stream to the pilot-scale distillation tower is shown in Table 5 below. For the purposes of comparing data to the pilot-scale tower, a stand-alone RADFRAC block with a total condenser was modeled, which in essence represented block 312 in FIG. 3. The simulations were performed assuming a total of 42 theoretical stages (40 in the tower and one each for boiler and condenser).

TABLE 5

| | FEED Analytical | OVERHEADS Analytical | BOTTOMS Analytical | FEED Simulation | OVERHEADS Simulation | BOTTOMS Simulation |
|---|---|---|---|---|---|---|
| FLOW RATE, lb/hr | 1.8 | 1.1 | 0.6985 | 1.8 | 1.14 | 0.650 |
| MASS FRACTION, wt % | | | | | | |
| Propylene | 0.287 | 0.462 | 0 | 0.287 | 0.449 | 0.000 |
| Propane | 0 | 0 | 0 | 0.000 | 0.000 | 0.000 |
| Isobutylene | 0.063 | 0.091 | 0 | 0.063 | 0.099 | 0.000 |
| N Butane | 0.008 | 0.011 | 0 | 0.008 | 0.013 | 0.000 |
| Methanol | 0.055 | 0.08 | 0 | 0.055 | 0.086 | 0.000 |
| Methyl Formate | 0.01 | 0.016 | 0 | 0.010 | 0.016 | 0.000 |
| N Pentane | 0.024 | 0.035 | 0 | 0.048 | 0.075 | 0.000 |
| Furan | 0.735 | 1.017 | 0 | 0.735 | 1.150 | 0.000 |
| Propylene Oxide | 60.445 | 95.166 | 0.016 | 60.445 | 94.562 | 0.000 |
| Propionaldehyde | 0.873 | 1.018 | 0.002 | 0.873 | 1.357 | 0.016 |
| 2 Methyl Pentane | 0.157 | 0.232 | 0 | 0.157 | 0.246 | 0.000 |
| Allyl Alcohol | 34.508 | 0.04 | 95.02 | 34.508 | 0.000 | 95.494 |
| N Propanol | 0.248 | 0 | 0 | 0.248 | 0.000 | 0.686 |
| Propylene Glycol | 0.08 | 0 | 0.2553 | 0.080 | 0.000 | 0.221 |
| Dipropylene Glycol | 0.043 | 0 | 0.1803 | 0.043 | 0.000 | 0.224 |
| Water (TCD) | 0.155 | 0.342 | 0 | 0.155 | 0.242 | 0.000 |
| Total | 97.691 | 98.51 | 95.4736 | 97.715 | 98.294 | 96.642 |

Example 3

Computer simulations were conducted using Aspen Plus® V7.3 to determine suitable feed locations for introducing the impure propylene oxide stream to the pilot-scale distillation tower. A first simulation case considered feeding the impure propylene oxide stream to the reflux drum of the pilot scale tower. In this case, the impure propylene oxide stream was co-fed with refined propylene oxide, providing the flexibility of increasing or decreasing the amount of either of those two streams to meet the design production capacity. The first case considered a purge stream which is represented by stream 328 in FIG. 3. A second simulation case considered feeding the impure propylene oxide stream along with the isomerization product stream from the reactor at the feed tray of the distillation tower. The second case also considered a purge stream as described above. A third simulation case considered decreasing the quantity of purge from the second simulation case. This resulted in a net increase in the allyl alcohol yield, however, it also resulted in a decrease in concentration of propylene oxide in distillation tower overhead from about 87.5 wt % to about 83.6 wt %. In each of the abovementioned simulation cases, the feed tray was located at the $25^{th}$ theoretical stage. Additionally, in each of the simulation cases, the flow rate of the refined propylene oxide feed was maintained at 1600 lb/h (726 kg/h) and its location was not altered. The flow rate of the impure propylene oxide stream was 12,400 lb/h (5624 kg/h), resulting in a total flow rate of 14,000 lb/h (6350 kg/h) for the three simulation cases. The composition of the feed stream is shown in Table 5 as "Feed Simulation".

Table 6 summarizes the results from each simulation case.

TABLE 6

| | AA Yield (%) | Purge | PO Conc. Ovhd. Stream (wt. %) | Distillation Tower Duty | |
|---|---|---|---|---|---|
| | | | | Condenser | Reboiler |
| Simulation Case 1 | 88 | 250 lb/h (113 kg/h) | 82.62 | 2.1 MMBTU/hr (615.5 kW hr) | 13.6 MMBTU/hr (3986 kW hr) |
| Simulation Case 2 | 90 | 180 lb/h (81.7 kg/h) | 87.54 | 2.7 MMBTU/hr (791 kW hr) | 13.5 MMBTU/hr (3956 kW hr) |
| Simulation Case 3 | 91 | 50 lb/h (22.68 kg/h) | 83.60 | 2.6 MMBTU/hr (762 kW hr) | 13.6 MMBTU/hr (3986 kW hr) |

The results in Table 6 indicated that although feeding an impure propylene oxide stream at the reflux drum of the distillation tower is feasible, it resulted in lower allyl alcohol yield. This was due to a comparatively larger purge which had to be sustained for removing the lights that accumulated in the overhead stream. On the other hand, feeding an impure propylene oxide stream along with an isomerization product stream at Tray 25 of a distillation column resulted in an increase in allyl alcohol yield by about 2%, resulting in an overall allyl alcohol yield of about 90 wt. %.

To further improve allyl alcohol yield, the amount of purge was further decreased and results for that case are also shown in Table 6. Results indicated that a further decrease in the amount of purge increased the allyl alcohol yield, however, it resulted in a decrease in the concentration of propylene oxide in the overhead stream of the distillation column. To further determine equipment constraints, the distillation tower flooding, downcomer flooding, and heat duties calculated by ASPEN simulations for the condensers and reboilers for the three cases above were calculated and compared against the design. Those results are summarized in Table 7.

TABLE 7

| | Distillation Tower | | | |
|---|---|---|---|---|
| | Flooding | | Utilization | |
| | Tray | Downcomer | Condenser | Reboiler |
| Simulation Case 1 | 71% | 89% | 54% | 74% |
| Simulation Case 2 | 72% | 90% | 69% | 73% |
| Simulation Case 3 | 75% | 95% | 67% | 73% |

The results shown in Table 6 and Table 7 suggest that lower flow rates for the purge stream may come at the cost of increased downcomer flooding and lower concentration of propylene oxide in the first column overhead stream. While the foregoing is directed to embodiments of the present disclosure, further embodiments of the disclosure may be devised without departing from the scope of the present disclosure.

What is claimed is:

1. A process comprising:
   contacting a propylene oxide stream with an isomerization catalyst comprising lithium phosphate under isomerization conditions sufficient to form an isomerization product stream comprising allyl alcohol,
   recovering allyl alcohol from the isomerization product stream to form an allyl alcohol stream comprising introducing the isomerization product stream into a first column adapted to separate propylene oxide from allyl alcohol comprising a top a bottom, and in the range of 36 to 49 theoretical stages, and wherein the impure propylene oxide stream is introduced to the first column at one or more theoretical stages in the range of the $17^{th}$ to the $28^{th}$ stage, counted from the bottom to the top of the first column,
   forming a first overhead stream comprising propylene oxide and a first bottoms stream comprising allyl alcohol and purging at least a portion of the first overhead stream to form a first purge stream when the concentration of propylene oxide in the first overhead stream is 90 wt. % or less, based on the total weight of the first overhead stream; and
   transferring the first bottoms stream to a second column adapted to separate methanol from allyl alcohol and form a second overhead stream comprising methanol and a second bottoms stream comprising allyl alcohol;
   contacting the allyl alcohol stream with a hydroformylation catalyst in the presence of a gas stream comprising carbon monoxide and hydrogen under hydroformylation conditions sufficient to form a hydroformylation product comprising a hydrogenation feed comprising a butane diol intermediate; and
   contacting the hydrogenation feed comprising the butane diol intermediate with hydrogenation catalyst in the presence of hydrogen under hydrogenation conditions comprising the hydrogenation catalyst contacting the hydrogenation feed at a concentration of 0.1-15 wt. % to form a hydrogenation product stream comprising 1,4-butane diol;

wherein the propylene oxide stream comprises a total impurity concentration of at least 100 ppm.

2. The process of claim 1, wherein the propylene oxide stream contacts the isomerization catalyst within an isomerization reactor and the recovering comprises:

introducing the isomerization product stream into a first column adapted to separate methanol from allyl alcohol and form a first overhead stream comprising methanol and propylene oxide and a first bottoms stream comprising allyl alcohol;

transferring the first overhead stream to a second column adapted to separate methanol from propylene oxide and form a second overhead stream comprising propylene oxide and a second bottoms stream comprising methanol; and transferring the second overhead stream to the isomerization reactor.

3. The process of claim 2, wherein the first bottoms stream comprises less than 25 ppm methanol.

4. The process of claim 2, wherein the second bottoms stream comprises less than 25 ppm methanol.

5. The process of claim 1, wherein the propylene oxide stream comprises a methyl formate concentration in a range of 0 wt. % to 1 wt. % based on the total weight of the propylene oxide stream.

6. The process of claim 1, wherein the propylene oxide stream comprises a methanol concentration in a range of 0 wt. % to 5 wt. % based on the total weight of the propylene oxide stream.

7. The process of claim 1, wherein the propylene oxide stream comprises an acetone concentration in a range of 0 wt. % to 20 wt. % based on the total weight of the propylene oxide stream.

8. The process of claim 1, wherein the propylene oxide stream comprises a water concentration in a range of 0 wt. % to 5 wt. % based on the total weight of the propylene oxide stream.

9. The process of claim 1, wherein the propylene oxide stream comprises a propionaldehyde concentration in a range of 0 wt. % to 1 wt. % based on the total weight of the propylene oxide stream.

10. The process of claim 1, wherein the isomerization conditions comprise an isomerization temperature in a range of 200° C. to 300° C. and an isomerization pressure in a range of 0 psig (0 Pa) to 30 psig (206,843 Pa).

11. The process of claim 1, wherein the isomerization catalyst comprises lithium phosphate.

12. The process of claim 1, wherein the recovering allyl alcohol comprises separating methanol from the allyl alcohol to form the allyl alcohol stream, wherein the allyl alcohol stream comprises less than 25 ppm methanol.

13. The process of claim 1 wherein the purging is a continuous operation.

14. The process of claim 1, wherein the hydrogenation catalyst contacts the hydrogenation feed at a concentration of 0.2-10 wt. %.

15. The process of claim 1 wherein the purging is a batch operation.

* * * * *

UNITED STATES PATENT AND TRADEMARK OFFICE
CERTIFICATE OF CORRECTION

PATENT NO. : 9,914,684 B2
APPLICATION NO. : 15/352771
DATED : March 13, 2018
INVENTOR(S) : Gaur et al.

Page 1 of 1

It is certified that error appears in the above-identified patent and that said Letters Patent is hereby corrected as shown below:

In the Specification

In Column 6, Line 10, after "one" insert -- or --.
In Column 6, Line 58, delete "Therminol*55," and insert -- Therminol®55, --.
In Column 16, Line 24, delete "was designed was designed" and insert -- was designed --.
In Column 19, Line 4, delete "pilot scale" and insert -- pilot-scale --.

In the Claims

In Column 22, Claim 13, Line 25, after "1" insert -- , --.
In Column 22, Claim 15, Line 30, after "1" insert -- , --.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*